US006575024B2

(12) United States Patent
Sinnett

(10) Patent No.: US 6,575,024 B2
(45) Date of Patent: Jun. 10, 2003

(54) APPARATUS AND METHOD FOR TESTING TIRES AND CALIBRATING FLAT BELT TIRE TESTING MACHINES

(75) Inventor: Jay C. Sinnett, Greenville, SC (US)

(73) Assignee: Michelin Recherche et Technique S.A., Granges-Paccot (CH)

( * ) Notice: Subject to any disclaimer, the term of this patent is extended or adjusted under 35 U.S.C. 154(b) by 0 days.

(21) Appl. No.: 09/968,683

(22) Filed: Oct. 1, 2001

(65) Prior Publication Data

US 2002/0104366 A1 Aug. 8, 2002

Related U.S. Application Data

(60) Provisional application No. 60/253,582, filed on Nov. 28, 2000.

(51) Int. Cl.[7] .............................................. E01C 23/00
(52) U.S. Cl. ...................................................... 73/146
(58) Field of Search .................................. 73/146, 9, 8

(56) References Cited

U.S. PATENT DOCUMENTS

| 4,238,954 A | | 12/1980 | Langer |
| 4,324,128 A | * | 4/1982 | Langer ........................... 73/8 |
| 4,344,324 A | | 8/1982 | Langer |
| 4,593,557 A | * | 6/1986 | Oblizajek et al. ............. 73/146 |
| 4,640,138 A | | 2/1987 | Meyer et al. |

OTHER PUBLICATIONS

Flat–Trac® Tire Test System Service Manual, Section 1, pp. 1–57 and Section 6, pp. 1–39, 1992.

* cited by examiner

Primary Examiner—Hezron Williams
Assistant Examiner—Charlene Dickens
(74) Attorney, Agent, or Firm—Dority & Manning, PA

(57) ABSTRACT

A machine, apparatus and method for testing tires with increased accuracy and reliability is disclosed. A flat belt tire tester employs a wheel and tire to be tested about an axis, whereby the tire is positioned above and upon the surface of a flat belt. A spindle and/or spindle extension is used for calibrating the machine, and forces are applied in a mechanical couple, providing a resulting force that is acceptable for calibration purposes. Once calibrated, the machine is capable of more reliably testing tires with accurate results. A numerical matrix is constructed by taking force measurements along each axis in a three axis system (X, Y and Z axes). An apparatus for reliably calibrating the machine and correcting for slight deviations (i.e., errors) in transducer readings by constructing an accurate matrix of correction factors is disclosed.

17 Claims, 6 Drawing Sheets

APPARATUS AND METHOD FOR TESTING TIRES AND CALIBRATING FLAT BELT TIRE TESTING MACHINES

CROSS-REFERENCE TO RELATED APPLICATIONS

This patent application claims priority to an earlier filed U.S. provisional patent application Ser. No. 60/253,582 filed on Nov. 28, 2000.

FIELD OF THE INVENTION

The present invention relates to tire testing machines utilizing a flat belt to simulate a road surface, and in particular, the invention relates to apparatus and methods for accurately calibrating such machines.

BACKGROUND OF THE INVENTION

Generating an improved tire design requires reliable testing equipment to measure tire performance under various load conditions. Tire testing machines have been used to evaluate tires under various load conditions to accurately determine the performance of various tire designs, under numerous conditions of tread wear, speed, load, and the like. Such testing may include low force static testing or high force dynamic testing.

One testing machine that has proved useful in such development work is the MTS Flat-Trac® machine which is sold commercially by MTS Systems Corporation of Minneapolis, Minn. Such machines are adapted for testing passenger car and light truck tires under a wide range of conditions. This particular testing machine, and other machines like it, use a simulated flat surface roadway. The machines control speed, radial force, radial position, slip angle, camber angle, inflation pressure, and spindle torque. Such testing machines facilitate the measurement of various forces acting upon the tire.

To obtain accurate data on tire performance, it is absolutely critical that the force sensing mechanism within the machine, comprising an electronic transducer, accurately measure and record the forces and moments exerted during testing in three axes—the X axis, Y axis and Z axis. Accurate measurement of force and moment vectors in each of the three axes depends upon a reliable and precise means and apparatus for performing a force and moment transducer calibration to generate an internal matrix data set that can be used by the machine controller in calculating corrected results. This corrective data set, or correction matrix, then may be used to compensate for crosstalk between the various transducer elements (or parts) within the force and moment transducer during testing.

At least two United States patents are directed to flat belt tire tester machines that provide for mounting a wheel and tire to be tested about an axis positioned above a flat rotating belt. U.S. Pat. Nos. 4,238,954 and 4,344,324 to Langer (collectively the "Langer patent(s)") each are directed to such a flat belt tire tester.

Multi-axis transducers have the capability to provide five or six measurements including moments and axial force measurements in the three principal axes (X, Y and Z). Such transducers are known in the art. However, there is a need in such applications to reduce crosstalk, i.e. the undesirable changes in reading for one axis resulting from loads applied in another axis.

In the past, calibration typically has been accomplished by applying five load vectors (six vectors when the spindle drive option is installed) to the transducer while measuring and recording the crosstalk produced by the loads applied. Then, a computational method has been employed to generate a calibration matrix file and interaction matrix from the recorded parameters.

Unfortunately, existing means of calibration have been significantly limited in the degree of precision that can be obtained in the measurement of forces acting upon the transducer, thus limiting the overall accuracy and reliability of the machine and its measurement of tire forces and tire responses. It is fundamental that a machine measurement can be only as accurate as the means used to calibrate the machine.

There are several disadvantages with such calibration methods. In the $M_z$ axis calibration, there is an undesirable longitudinal force applied simultaneously with the aligning torque during calibration, so that the measurement taken during calibration is not a pure measurement. In the $F_z$ axis calibration, there is a mechanical coupling that may undesirably permit $M_z$ torque to be introduced, through friction, creating an erroneous value for $M_z$ crosstalk compensation.

What is needed in the industry is a calibration method and apparatus that provides the highest possible level of accuracy and the slightest possible chance of introducing erroneous off-axis (i.e. crosstalk) forces or moments during the calibration procedure.

SUMMARY OF THE INVENTION

The present invention relates to improving tire testing machine accuracy through improved calibration apparatus and methods. Improvements to existing apparatus for calibrating a testing machine transducer are provided in the invention.

The transducer is capable of measuring load forces and moments in three perpendicular intersecting axes, the first axis comprising a longitudinal axis, the second axis comprising a lateral axis, and the third axis comprising a steer axis. Furthermore, a spindle with extension is aligned along the lateral axis and operably connected to the transducer.

During calibration, a spindle extension is connected to the spindle, which is located within the housing of the tire testing machine. The spindle extension includes a first location corresponding to the spindle axis/steer axis intersection point and a second location upon the spindle axis. The second location is typically provided at a predetermined distance from the first location. In the invention, an improved procedure for calibrating aligning torque or moment around the z axis (i.e., steer axis) ($M_z$) is provided. This method employs a mechanical couple.

In one application of the invention, first and second load members are provided, each of the first and second load members having a proximal end adapted for connection to the spindle and a distal end adapted for receiving a predetermined weight. The first load member is connected to the spindle extension at the first location, and the second load member is connected to the spindle extension at the second location. The first load member and the second load member together comprise a mechanical couple, such that a first force exerted upon the first load member by a first weight, and a second force exerted upon the second load member by a second weight, are intended to be equal. Thus, the first force and the second force act equally, but in opposite directions.

Furthermore, in other aspects of the invention, an improved method for isolating the normal force along the steer axis (i.e., $F_z$) is provided. In the latter case, an air bearing is used in connection with a load cell strut, wherein the load cell strut has been adapted for transmitting forces along the steer axis between the spindle and the air bearing. A friction reduction means is adapted for reducing the frictional contact between the load cell strut and the spindle. An air bearing comprising a load cell, a load cell strut, and a friction reduction means (or low-friction yoke) is adapted for reducing frictional contact between the load cell strut and a spindle extension.

BRIEF DESCRIPTION OF THE DRAWINGS

A full and enabling disclosure of this invention, including the best mode shown to one of ordinary skill in the art, is set forth in this specification. The following Figures illustrate the invention.

DETAILED DESCRIPTION OF THE INVENTION

Reference now will be made to the embodiments of the invention, one or more examples of which are set forth below. Each example is provided by way of explanation of the invention, not as a limitation of the invention. In fact, it will be apparent to those skilled in the art that various modifications and variations can be made in this invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention, which broader aspects are embodied in the exemplary constructions.

In general, when a tire rolling in one direction is acted upon by a steering force to steer it to another direction, the tire has an inherent capacity or ability to apply a restoring moment to steer back into the direction from which it came. This restoring force is sometimes referred to as an aligning torque.

Original equipment automobile manufacturers typically provide specific target values and tolerance ranges for various force parameters. For example, specific values of aligning torque are deemed acceptable for passenger tires, and tires falling outside of these specific stated ranges may be rejected as unsatisfactory. Other physical factors associated with tires also are subject to relatively strict scrutiny, and industry-wide acceptable ranges have been established. It is therefore important to properly measure the forces generated by a tire when a load is applied to a tire in a specific axis or plane, so that it may accurately be determined if a tire is within the acceptable range.

In the past, there have been attempts to correlate various flat belt tire testing machines with each other using a control tire. A control tire is not an absolute standard, and therefore it cannot alone actually calibrate such machine. However, it can be used periodically to determine if the machine has varied or deviated from its previous setting. Control tires do not provide the opportunity to ascertain with certainty the absolute values of the forces which are being measured. A high degree of certainty is desirable in the testing of tires.

Figure 1:
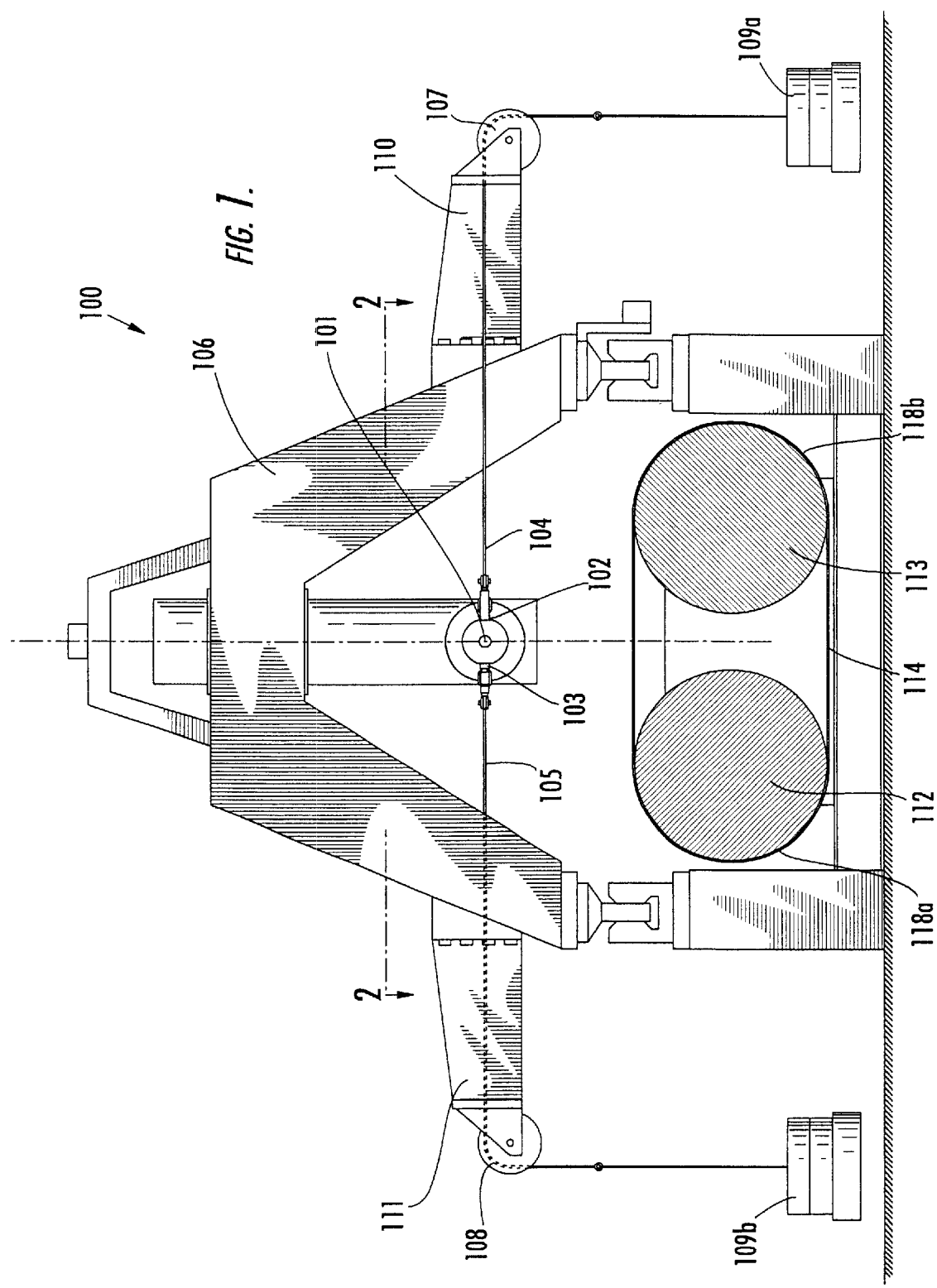
FIG. 1 is a side view showing an application of this invention comprising a calibration assembly and test set-up designed to provide calibration values for the aligning torque ($M_z$)

In FIG. 1, a tire testing machine 100 is shown configured for the measurement of the aligning torque $M_z$. The spindle extension 101 seen near the center of FIG. 1 is aligned along the lateral axis and operably connected to a spindle and a transducer (spindle and transducer are not shown in FIG. 1). The spindle extension 101 is releasably mounted upon the spindle near hub 116, and is employed when calibration is to be performed on the tire testing machine 100. A first location 102 and a second location 103 on the spindle are employed to secure the proximal ends of the first and second load members 104 and 105, respectively. The first load member 104 proceeds in front of the A-frame 106 to the right side of the Figure, where it passes over the first pulley 107. The second load member 105 proceeds from the second location 103 over the second pulley 108 and down towards the base of the machine. In the process of a complete calibration, the two load members will be connected both in front/back and in back/front configurations. The first load member 104 and the second load member 105 each are loaded with weights 109a and 109b during the testing procedure, as further described herein. The first pulley 107 and second pulley 108 are supported by a first outrigger 110 and a second outrigger 111, respectively.

As shown in FIG. 1, the first load member 104 and the second load member 105 include a proximal end that is adapted for connection to the spindle extension 101, and a distal end adapted for receiving a predetermined weight. The first location 102 and second location 103 are axially spaced on the spindle extension 101 to facilitate the formation of a mechanical couple. Furthermore, the first location 102 and second location 103 are located upon the same plane, which provides for respective forces acting in opposite directions.

The first load member 104 and the second load member 105 comprise a mechanical couple, such that a first force exerted upon the first load member by a first weight 109a, and a second force exerted upon the second load member 105 by a second weight 109b are intended to be equal. In that way, the first force and the second force act in opposite directions. By balancing the forces using a mechanical couple, it is possible to obtain much more accurate readings during the calibration, which results in a much more accurate set of corrective data that may be accumulated in a correction matrix.

The first load member 104 and second load member 105 may be comprised of essentially any material. However, it has been found that more accurate results may be obtained using a material that is flexible along substantially its entire length, and essentially the entire distance from the spindle to the weight. That is, some prior art calibration equipment has employed relatively stiff metallic wire for measuring force vectors pursuant to such calibrations. In general, such stiff wire is not an ideal material to use for such load members, because it is more likely to introduce undesirable forces in directions which are not in direct alignment with the path of the wire. These forces may introduce errors in calibration, which likewise reduces the overall accuracy and precision that can be obtained with the machine.

In the lower portion of FIG. 1, a first drum 112 and a second drum 113 are shown. The center frame 114a supports the first drum 112 and the second drum 113. A belt 114 simulates the road surface, and rotates around the external periphery of the drums, shown at 118a and 118b. Other components of the machine relating to the drive means are similar to that shown and previously discussed in connection with FIG. 1.

Figure 2:
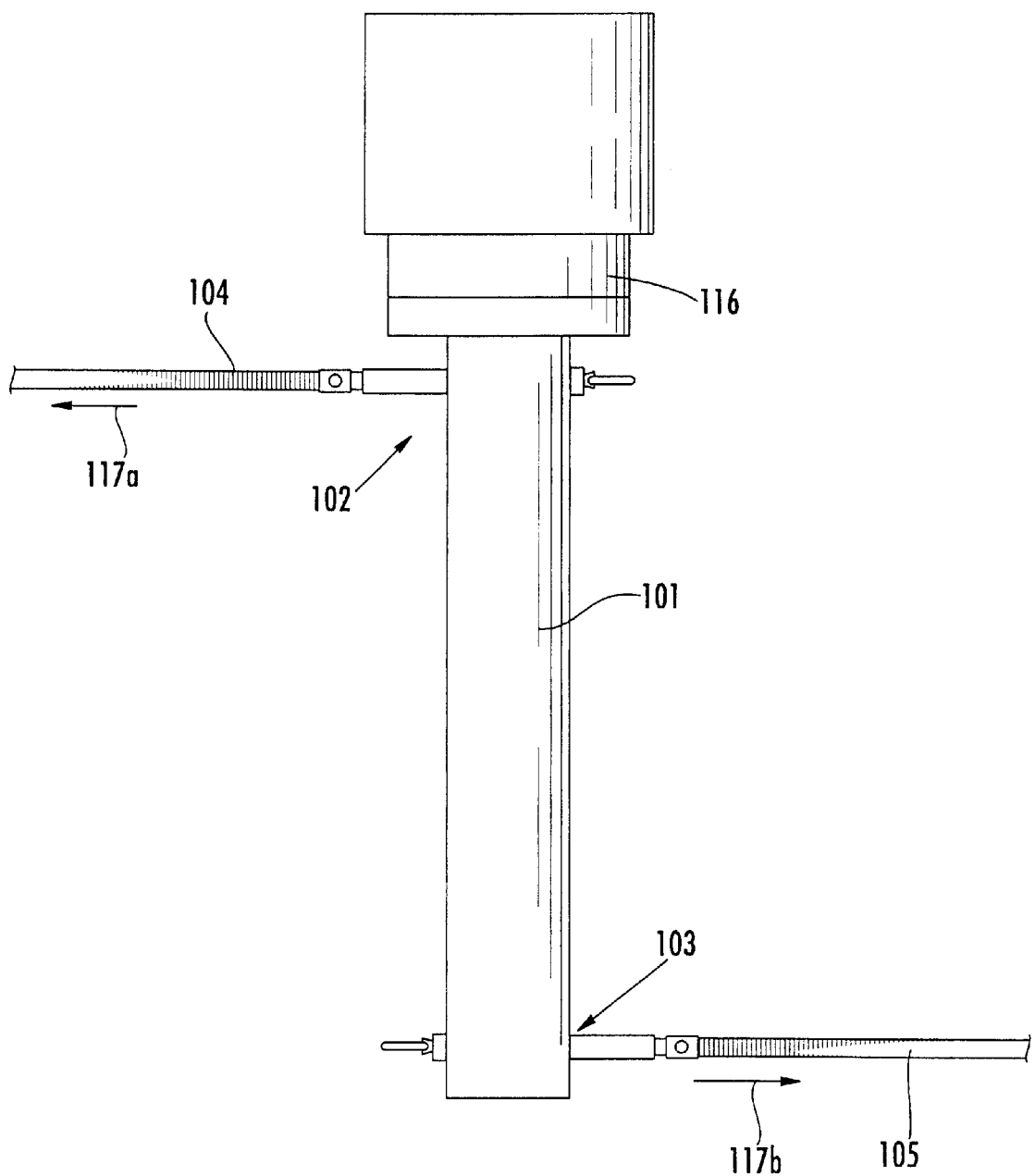
FIG. 2 provides a more detailed top view of the apparatus shown in FIG. 1 used to prepare a mechanical couple along the spindle extension corresponding to the configuration shown in FIG. 1.

In FIG. 2, a top view of the spindle extension 101 of FIG. 1 is shown, including a diagram showing the mechanical couple formed. FIG. 2 shows a top view taken along lines 2—2 (looking in the direction of the arrows) of FIG. 1. The hub 116 which fits over the transducer (not shown in FIG. 2) forms the base of the spindle extension 101 that extends outward from the hub 116. First load member 104 is shown attaching to the first location 102 while the second load member 105 attaches to the second location 103. At a later point during the calibration, load member 104 will be connected at second location 103 and second load member 105 will be connected at first location 102. The first load member 104 and the second load member 105 form a mechanical couple, and when loaded with weight, effectively cancel each other.

Preferably, the first load member 104 and the second load member 105 are formed of any material that is flexible enough to avoid introducing forces in any direction except the force direction arrows 117a and 117b. One material that has proved to work well is shim stock material, but many other materials would work equally as well. The invention is not limited to any particular material for use in a load member.

Figure 3:
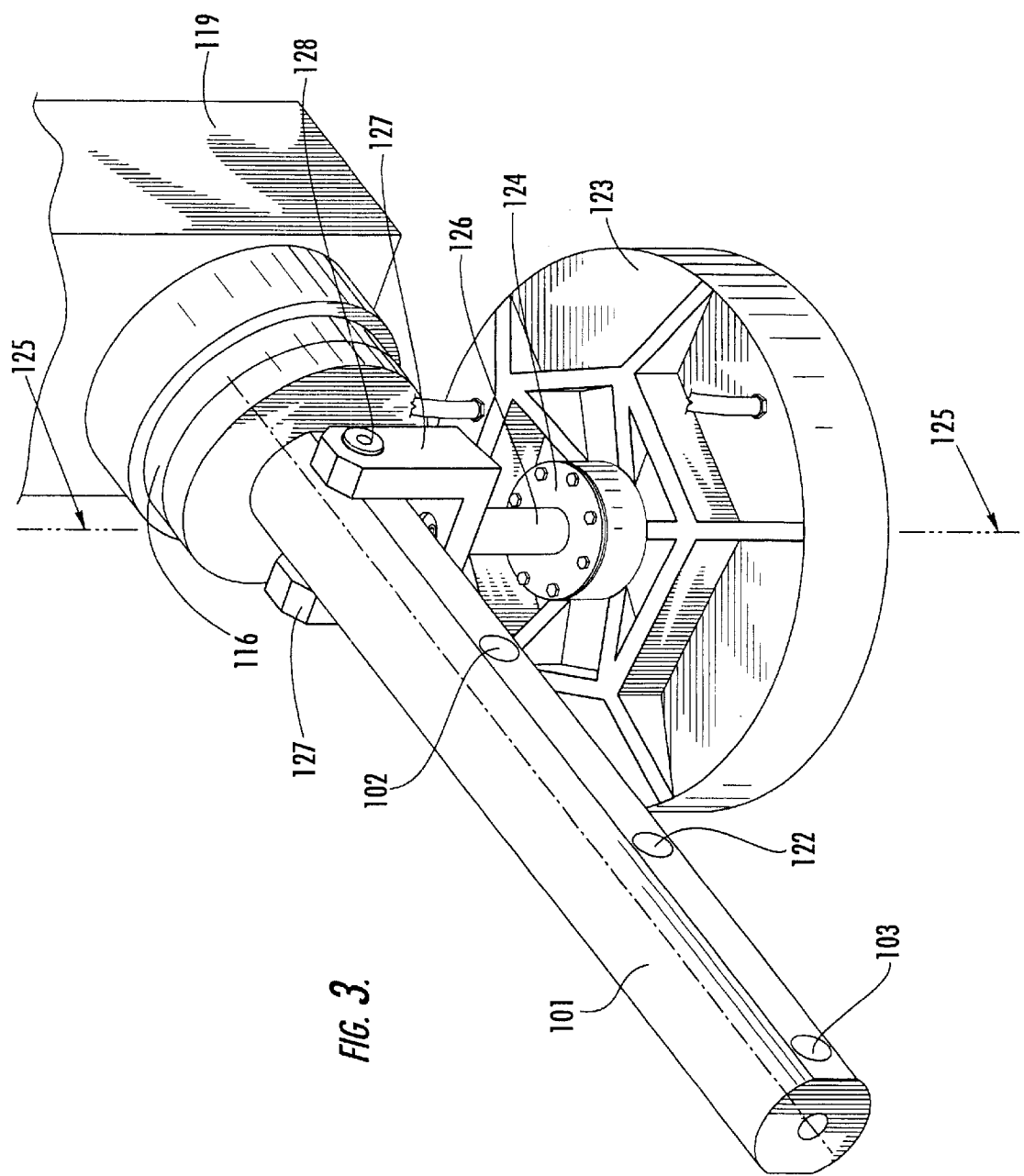
FIG. 3 reveals a perspective view of an alternate embodiment of the testing machine and calibration apparatus of the invention in which an air bearing is located upon the simulated roadway surface or belt in order to obtain calibration correction values for the normal force $F_z$ and the lateral force $F_y$.

In FIG. 3, a perspective view of an alternative embodiment of the invention is shown which comprises an assembly utilized to determine the normal force $F_z$ in a calibration procedure. This procedure results in a more accurate measurement using the machine in the testing of tires. An improved mechanical assembly is shown, as described below. In FIG. 3, a transducer housing 119 is shown attached to hub 116. A spindle extension 101 extends from the hub laterally, and a first location 102 and second location 103 are shown along the length of the spindle extension 101. Optionally, a third location 122 may be used in situations in which the force vector is to be of a different value.

An air bearing 123 is provided, which rests upon a granite plate on the surface of the belt 114. This apparatus is used to calibrate forces along the steer axis 125 as shown in FIG. 3. A load cell strut 126 is shown resting upon the upper surface of load cell 124. The load cell strut transmits forces to the load cell 124, which are measured by the load cell 124. The load cell strut 126 is connected on its upper end to friction reduction means 127, which in this particular embodiment is represented by a y-shaped low-friction yoke. The friction reduction means 127 (which may be comprised of a low-friction yoke 127) is connected to the spindle extension 101 by a shaft 128 that rests within anti-torque bearings to allow a substantially frictionless articulation of the low-friction yoke 127 as it spins freely with a minimum amount of friction upon top of the load cell strut 126.

Figure 4:
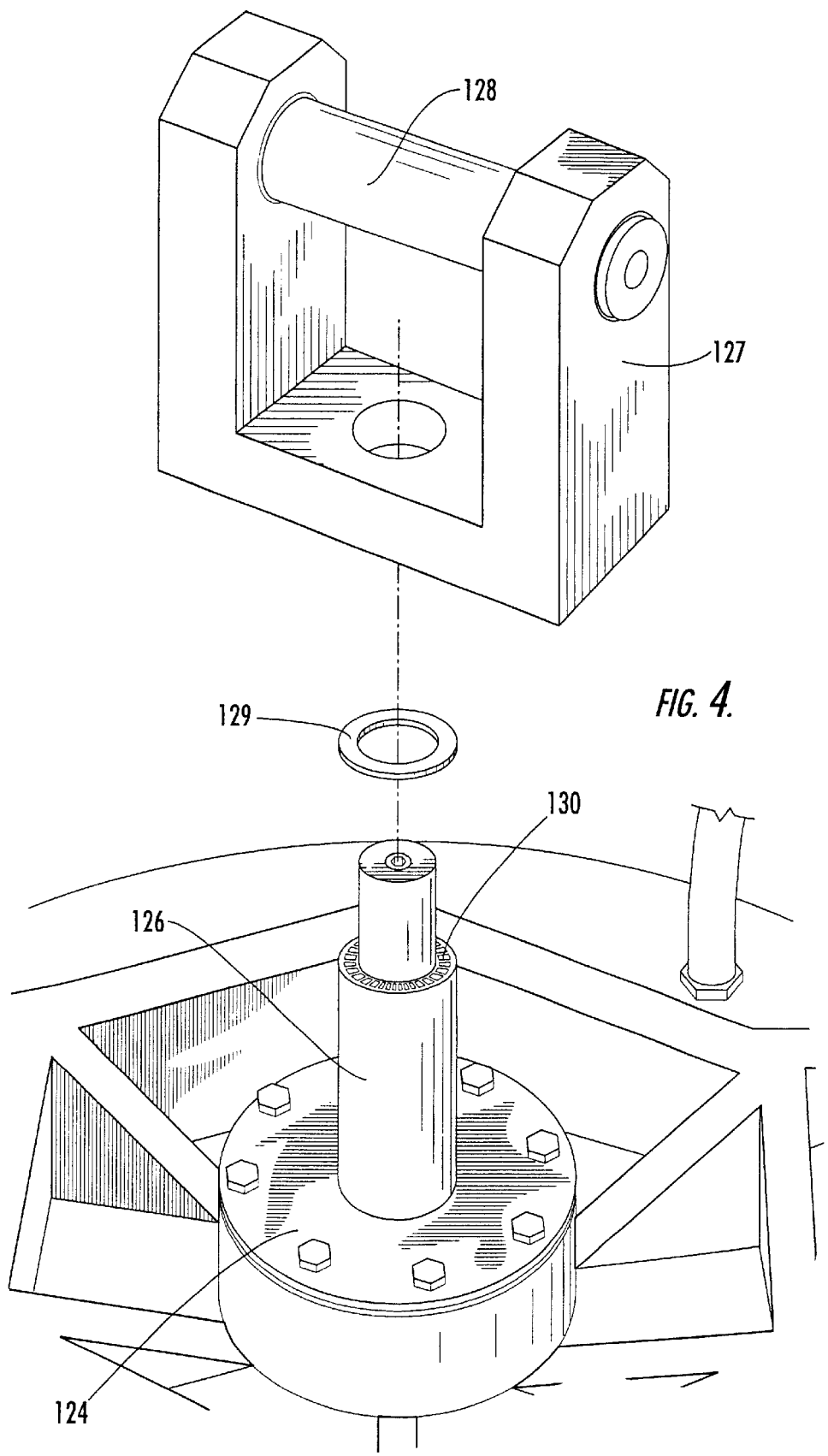
FIG. 4 shows a perspective view of the load cell strut used in one aspect of the invention as a friction reduction means for reducing frictional contact with the spindle.

FIG. 4 shows a perspective exploded view of a low-friction yoke 127 having a shaft 128 mounted thereon. The low-friction yoke 127 rests upon washer 129 that fits upon roller bearings 130 located around the periphery of the load cell strut 126 that rests upon load cell 124. This is one embodiment of the assembly that can be used in the application of the invention, and other mechanical means besides a low-friction yoke 127 could accomplish the same result, and are within the scope of the invention.

Figure 5:
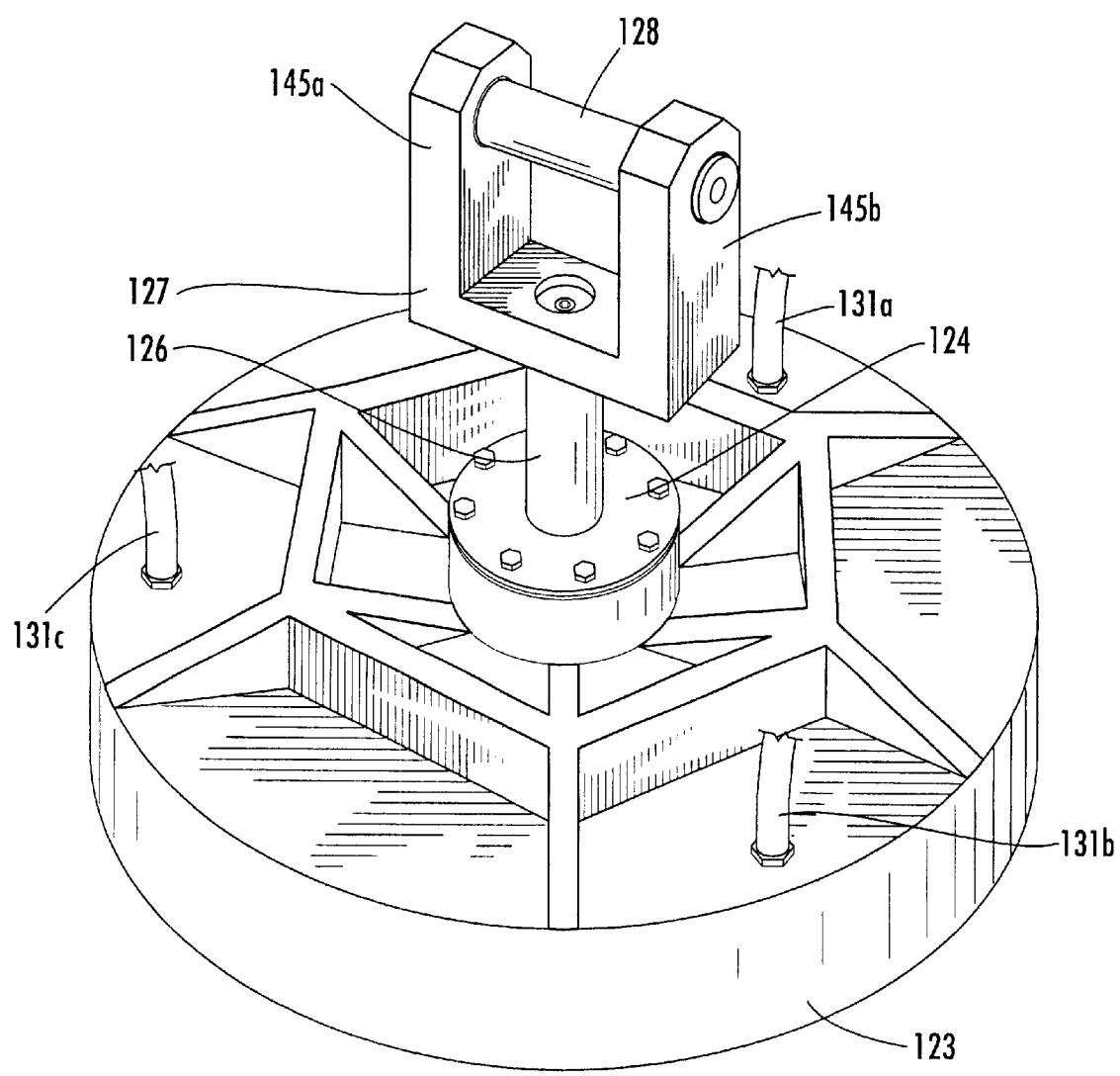
FIG. 5 reveals a perspective view of a low-friction yoke on a load cell strut that includes anti-torque bearings as a means for reducing friction in the collection of calibration data values.

FIG. 5 shows a perspective view of the apparatus as assembled upon the air bearing 123. Air hoses 131a–c provide compressed air which is released along the bottom surface of air bearing 123 to keep the air bearing 123 "floating" on top of a granite block (not shown) which itself rests upon the surface of the road simulation belt. The low-friction yoke 127 also comprises a first arm 145a and a second arm 145b which are adapted at their ends to receive the shaft 128. Load cell strut 126 connects the low-friction yoke 127 to the load cell 124.

Figure 6:
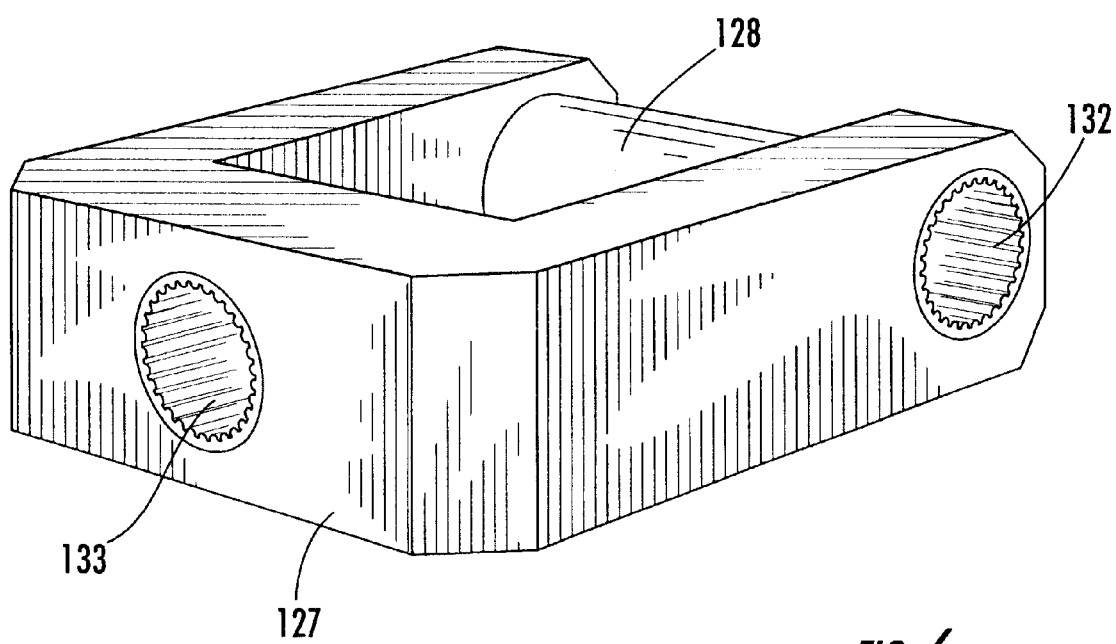
FIG. 6 is a perspective view that shows one embodiment of the invention using anti-torque bearings as a friction reduction means.

FIG. 6 shows a perspective view of the low-friction yoke 127 having shaft 128 which includes roller bearings 132 and 133 to avoid the undesirable introduction of forces in any direction other than the normal force $F_z$ during the operation of the testing apparatus. The invention is not limited to any particular type of roller bearing apparatus, but one roller bearing that may be employed in the invention is a bearing manufactured by the Torrington Company designated model number J-1416. The J-1416 roller bearing includes an inside diameter of about ⅞ inches, an outside diameter of about 1⅛ inches, with a width of about 1 inch. Other roller bearing sizes and types from other manufacturers could also be employed in the practice of the invention.

In the method of calibrating a flat belt tire testing machine, first the spindle extension 101 is mounted and aligned along the lateral axis in operable connection to the transducer (not shown). That is, the spindle extension 101 includes a first location 102 along the spindle extension 101 that corresponds to the spindle axis/steer axis intersection point. A second location 103 upon the spindle axis is located a predetermined distance from the first location 102. First, a first load member 104 is connected to the first location 102 on the spindle extension 101 along the spindle axis. Then, a second load member 105 is connected to a second location 103 on the spindle extension 101. Then, a first weight 109a is applied to the first load member 104 in a first direction. The next step includes applying a second weight 109b of approximately equal value to the first weight 109a to the second load member 105 in a second direction, which is opposite to the first direction. This is most easily seen in FIG. 1. Once weights are placed on each side, a mechanical couple is formed along the lateral axis. Then, it is possible to measure the forces generated in the steer axis and the longitudinal axis. Furthermore, data may be collected to form a matrix of corrective calibration values in both the steer axis and the longitudinal axis directions.

The following Tables give examples of how calibration measurements are used to generate and check the individual channel scale factors and the quality of the Correction Matrix. These Examples are only samples drawn from a larger set of data used for one calibration, but they are sufficient to demonstrate the utility of the claimed inventions. In particular, one may note the extremely good isolation present in the measurement transducer when measuring a pure $M_z$. If the calibration apparatus applied an impure input (such as combined Fx and Mz) then the transducer's quality would not be measured directly and the correction matrix would be compromised.

EXAMPLE 1

In this example, an applied moment $M_z$ that comprises aligning torque is measured. An equal amount of weight is placed simultaneously on both sides of the machine, as shown in FIG. 1. The following settings were employed:

Offset (m) 0.45

Equipment: Weight Hangers (empty hanger weighs about 2 kg)

Geometry: Slip Angle=0; Inclination Angle=0

Applied "zero" is performed with empty hangers installed. Furthermore, negative $M_z$ values are generated when weights are configured as shown in FIG. 2, while positive $M_z$ values are generated when load member 104 is connected at second location 103 and load member 105 is connected at first location 102. Several different weights are applied (always equally on both sides) to calibrate Mz. Values are generated and stored in a matrix as set forth in Table 1.

Calibration data for $M_z$, shown below in Tables 1 and 2, was generated using the apparatus shown in FIGS. 1 and 2.

The second group of readings below in Table 2 were taken with the apparatus configured as in FIG. 2 (negative $M_z$), while the first group of readings were taken with the left and right pull positions reversed from that shown in FIG. 2 (i.e. positive $M_z$).

The application of a pure $F_z$ force tends to create cross-talk readings in every other channel. In this case, it is of paramount importance that the mechanical components used to generate (and measure) the applied $F_z$ calibration force impart no other force or moment at all. For example, the correction matrix term for removing the cross-talk component of $M_z$ due to $F_z$ is −0.0009909; this is a very small number, yet it has a large influence on the "Plysteer Residual Aligning Torque" measurement that vehicle manufacturers specify to very tight tolerance limits. If the mechanical components of the calibration apparatus introduced any $M_z$ when it should be zero, then this term in the correction matrix would be incorrect.

In the following Tables 1 and 3A, the "Measured Forces and Moments (Uncorrected)" values are provided in engineering units of Newtons and Newtonmeters The values were calculated from raw A-to-D counts by first subtracting the tare and then multiplying by an appropriate scale factor (different for each channel). The data for each reading in the entire calibration were combined to generate the correction matrix of Table 4.

EXAMPLE 2

The applied force measured in the direction $F_z$ is accomplished in this example. Negative numbers represent the force of the tire "pushing on road." Results of this example are shown in Tables 3A and 3B.

Equipment: Calibration Loadcell and air bearing as shown.

Geometry: SA (slip angle)=0, IA (Inclination Angle)=0

TABLE 1

| Fx | Fy | Fz | Mx | Mz |
|---|---|---|---|---|
| True (Applied) Forces & Moments | | | | |
| 0.0 | 0 | 0 | 0.0 | 0.00 |
| 0.0 | 0 | 0 | 0.0 | 88.26 |
| 0.0 | 0 | 0 | 0.0 | 176.52 |
| 0.0 | 0 | 0 | 0.0 | 264.78 |
| 0.0 | 0 | 0 | 0.0 | 441.30 |
| 0.0 | 0 | 0 | 0.0 | 264.78 |
| 0.0 | 0 | 0 | 0.0 | 176.52 |
| 0.0 | 0 | 0 | 0.0 | 88.26 |
| 0.0 | 0 | 0 | 0.0 | 0.00 |
| 0.0 | 0 | 0 | 0.0 | 0.00 |
| 0.0 | 0 | 0 | 0.0 | −88.26 |
| 0.0 | 0 | 0 | 0.0 | −176.52 |
| 0.0 | 0 | 0 | 0.0 | −264.78 |
| 0.0 | 0 | 0 | 0.0 | −441.30 |
| 0.0 | 0 | 0 | 0.0 | −264.78 |
| 0.0 | 0 | 0 | 0.0 | −176.52 |
| 0.0 | 0 | 0 | 0.0 | −88.26 |
| 0.0 | 0 | 0 | 0.0 | 0.00 |
| Measured Forces & Moments (Uncorrected) | | | | |
| −1.3 | 0 | 0 | 0.0 | −0.12 |
| 0.3 | 0 | 0 | 0.0 | 88.11 |
| 1.8 | 0 | 0 | 0.0 | 176.34 |
| 2.9 | −5 | 0 | 0.0 | 264.80 |
| 5.0 | −5 | 0 | −2.4 | 441.26 |
| 3.9 | 0 | 0 | −2.4 | 265.28 |
| 2.9 | 0 | 0 | 0.0 | 177.05 |
| 0.8 | 0 | 0 | 0.0 | 88.35 |
| 1.3 | 0 | 0 | 0.0 | 0.12 |
| 0.0 | 0 | 0 | 0.0 | 0.12 |
| −1.6 | 5 | 0 | 0.0 | −87.87 |
| −2.6 | 5 | 0 | 0.0 | −176.10 |
| −4.2 | 5 | 0 | 2.4 | −264.33 |
| −6.8 | 10 | 0 | 2.4 | −441.26 |
| −4.2 | 5 | 0 | 2.4 | −264.57 |
| −2.1 | 5 | 0 | 0.0 | −177.05 |
| −1.6 | 5 | 0 | 0.0 | −88.58 |
| 0.0 | 0 | 0 | 0.0 | −0.12 |

TABLE 2

| Fx | Fy | Fz | Mx | Mz |
|---|---|---|---|---|
| Corrected (Post-Matrix) Forces & Moments | | | | |
| −1.3 | 0 | 0 | 0.0 | −0.11 |
| −0.9 | 1 | 0 | 0.4 | 88.11 |
| −0.6 | 3 | −1 | 0.9 | 176.32 |
| −0.8 | −1 | −1 | 1.3 | 264.78 |
| −1.0 | 2 | 5 | −0.2 | 441.22 |
| 0.4 | 4 | −1 | −1.1 | 265.25 |
| 0.5 | 3 | −1 | 0.9 | 177.03 |
| −0.4 | 1 | 0 | 0.4 | 88.34 |
| 1.3 | 0 | 0 | 0.0 | 0.11 |
| 0.0 | 0 | 0 | 0.0 | 0.12 |
| −0.3 | 4 | 0 | −0.4 | −87.86 |
| −0.2 | 2 | 1 | −0.8 | −176.08 |
| −0.6 | 1 | 1 | 1.1 | −264.31 |
| −0.8 | 3 | 1 | 0.3 | −441.22 |
| −0.6 | 1 | 1 | 1.1 | −264.54 |
| 0.4 | 2 | 1 | −0.9 | −177.03 |
| −0.3 | 4 | 0 | −0.4 | −88.57 |
| 0.0 | 0 | 0 | 0.0 | −0.12 |

TABLE 2-continued

| Fx | Fy | Fz | Mx | Mz |
|---|---|---|---|---|
| Errors, % of Full Scale | | | | |
| −0.13% | 0.00% | 0.00% | 0.00% | −0.01% |
| −0.09% | 0.01% | 0.00% | 0.00% | −0.02% |
| −0.06% | 0.01% | 0.00% | 0.01% | −0.02% |
| −0.08% | 0.00% | 0.00% | 0.01% | 0.00% |
| −0.10% | 0.01% | 0.02% | 0.00% | −0.01% |
| 0.04% | 0.02% | 0.00% | −0.01% | 0.05% |
| 0.05% | 0.01% | 0.00% | 0.01% | 0.05% |
| −0.04% | 0.01% | 0.00% | 0.00% | 0.01% |
| 0.13% | 0.00% | 0.00% | 0.00% | 0.01% |
| 0.00% | 0.00% | 0.00% | 0.00% | 0.01% |
| −0.03% | 0.02% | 0.00% | 0.00% | 0.04% |
| −0.02% | 0.01% | 0.00% | −0.01% | 0.04% |
| −0.06% | 0.00% | 0.00% | 0.01% | 0.05% |
| −0.08% | 0.01% | 0.01% | 0.00% | 0.01% |
| −0.06% | 0.00% | 0.00% | 0.01% | 0.02% |
| 0.04% | 0.01% | 0.00% | −0.01% | −0.05% |
| −0.03% | 0.02% | 0.00% | 0.00% | −0.03% |
| 0.00% | 0.00% | 0.00% | 0.00% | −0.01% |

The data in Tables 3A–3B comprise examples of $F_z$ calibration. Reference is made to FIG. 3.

TABLE 3A

| Fx | Fy | Fz | Mx | Mz |
|---|---|---|---|---|
| True (Applied) Forces & Moments | | | | |
| 0.0 | 0 | 0 | 0.0 | 0.00 |
| 0.0 | 0 | −4043 | 0.0 | 0.00 |
| 0.0 | 0 | −7963 | 0.0 | 0.00 |
| 0.0 | 0 | −11927 | 0.0 | 0.00 |
| 0.0 | 0 | −15902 | 0.0 | 0.00 |
| 0.0 | 0 | −19914 | 0.0 | 0.00 |
| 0.0 | 0 | −16000 | 0.0 | 0.00 |
| 0.0 | 0 | −11988 | 0.0 | 0.00 |
| 0.0 | 0 | −7945 | 0.0 | 0.00 |
| 0.0 | 0 | −3982 | 0.0 | 0.00 |
| 0.0 | 0 | 0 | 0.0 | 0.00 |

TABLE 3A-continued

| Fx | Fy | Fz | Mx | Mz |
|---|---|---|---|---|
| Measured Forces & Moments (Uncorrected) | | | | |
| −0.3 | 0 | 0 | 0.0 | 0.00 |
| −37.8 | −10 | −4050 | 12.1 | −4.03 |
| −72.7 | −20 | −7969 | 24.2 | −8.06 |
| −108.1 | −31 | −11926 | 38.7 | −12.10 |
| −143.0 | −41 | −15902 | 50.8 | −17.08 |
| −179.0 | −51 | −19921 | 62.8 | −22.53 |
| −144.1 | −41 | −16001 | 50.8 | −15.65 |
| −109.2 | −31 | −11988 | 38.7 | −11.38 |
| −72.7 | −20 | −7945 | 24.2 | −7.59 |
| −37.8 | −10 | −3988 | 12.1 | −3.79 |
| 0.3 | 0 | 0 | 0.0 | 0.00 |

TABLE 3B

| Fx | Fy | Fz | Mx | Mz |
|---|---|---|---|---|
| Corrected (Post-Matrix) Forces & Moments | | | | |
| −0.3 | 0 | 0 | 0.0 | 0.00 |
| −1.0 | 2 | −4049 | −1.0 | 0.19 |
| −0.4 | 3 | −7969 | −1.5 | 0.23 |
| 0.0 | 4 | −11926 | 0.2 | 0.30 |
| 1.2 | 6 | −15901 | −0.5 | −0.56 |
| 1.7 | 7 | −19919 | −1.4 | −1.83 |
| 1.0 | 6 | −16000 | −0.9 | 0.97 |
| −0.5 | 5 | −11987 | 0.0 | 1.08 |
| −0.6 | 3 | −7944 | −1.4 | 0.68 |
| −1.6 | 2 | −3988 | −0.8 | 0.36 |
| 0.3 | 0 | 0 | 0.0 | −0.00 |
| Errors, Percentage of Full Scale | | | | |
| −0.03% | 0.00% | 0.00% | 0.00% | 0.00% |
| −0.10% | 0.01% | −0.03% | −0.01% | 0.02% |
| −0.04% | 0.01% | −0.02% | −0.02% | 0.02% |
| 0.00% | 0.02% | 0.00% | 0.00% | 0.03% |
| 0.12% | 0.03% | 0.01% | −0.01% | −0.06% |
| 0.17% | 0.04% | −0.02% | −0.01% | −0.18% |
| 0.10% | 0.03% | 0.00% | −0.01% | 0.10% |
| −0.05% | 0.02% | 0.00% | 0.00% | 0.11% |
| −0.06% | 0.01% | 0.00% | −0.01% | 0.07% |
| −0.16% | 0.01% | −0.02% | −0.01% | 0.04% |
| 0.03% | 0.00% | 0.00% | 0.00% | 0.00% |

The examples given demonstrate the use of the claimed inventions. The correction matrix of Table 4 was created by performing a complete 5-axis calibration.

TABLE 4

Correction Matrix

| | To Fx | To Fy | To Fz | To Mx | To Mz |
|---|---|---|---|---|---|
| From Fx | 1.0000236 | −0.0086012 | 0.0000137 | −0.0022746 | −0.0063786 |
| From Fy | 0.0110084 | 1.0000876 | 0.0013057 | 0.0002048 | −0.0002796 |
| From Fz | −0.0091546 | −0.0028873 | 0.9999132 | 0.0031958 | −0.0009909 |
| From Mx | −0.0227524 | −0.0041331 | −0.0049689 | 0.9859320 | −0.0031750 |
| From Mz | −0.0134657 | 0.0164866 | −0.0033028 | 0.0048510 | 0.9999757 |

Table 4 provides the correction matrix. Numbers provided in Table 4 on the principal diagonal (upper left corner to lower right corner) are close to 1. This is a natural consequence of the design of the matrix. That is, if there were no cross-talk between channels at all, then the numbers in the diagonal would all be exactly 1.00000 and all the other numbers would be zero. The matrix may be employed to manually or automatically correct data to obtain more accurate and reliable calibration of a tire testing apparatus.

It is understood by one of ordinary skill in the art that the present discussion is a description of exemplary embodiments only, and is not intended as limiting the broader aspects of the present invention, which broader aspects are embodied in the exemplary constructions. The invention is shown by example in the appended claims.

What is claimed is:

1. An apparatus for calibrating a tire testing machine using a mechanical couple, the machine providing load vectors in three perpendicular intersecting axes, the first axis comprising a longitudinal axis, the second axis comprising a lateral axis and the third axis comprising a steer axis, wherein the apparatus comprises:
    (a) a spindle extension aligned along the lateral axis, the spindle extension having:
        a first location corresponding to the spindle axis/steer axis intersection point; and
        a second location, the second location being positioned a predetermined distance from the first location;
    (b) first and second load members, each of the first and second load members having a proximal end adapted for connection to the spindle extension and a distal end adapted for receiving a predetermined weight, the first load member being connected to the spindle extension at the first location, and the second load member being connected to the spindle extension at the second location, and
    (c) wherein the first load member and the second load member together comprise a mechanical couple, such that a first force exerted upon the first load member by a first weight and a second force exerted upon the second load member by a second weight are substantially equal, whereby the first force and the second force act in opposite directions.

2. The apparatus of claim 1 wherein the first load member is flexible along its length, and extends substantially the entire distance from the spindle extension to the first weight.

3. The apparatus of claim 1 wherein the second load member is flexible along its length and extends substantially the entire distance from the second location of the spindle extension to the second weight.

4. The apparatus of claim 1 further comprising a first outrigger which is adapted for supporting the first load member.

5. The apparatus of claim 4 further comprising a second outrigger adapted for supporting the second load member.

6. The apparatus of claim 4 in which the first outrigger comprises a first pulley adapted to support the first load member.

7. The apparatus of claim 5 in which the second outrigger further comprises a second pulley adapted for supporting the second load member.

8. An apparatus for calibrating a tire testing machine, wherein the machine is capable of isolating and measuring load forces in three perpendicular intersecting axes, the first axis comprising a longitudinal axis, the second axis comprising a lateral axis, and the third axis comprising a steer axis, the apparatus being configured for cooperating with a transducer configured for detecting forces along said axes comprising:
    (a) a spindle extension aligned along the lateral axis and operably connected to a transducer;
    (b) an air bearing;
    (c) a load cell strut, the strut being connected to the air bearing and adapted for transmitting forces along the steer axis between the spindle extension and the air bearing; and
    (d) a low friction yoke adapted for reducing frictional contact between the load cell strut and the spindle extension, the low friction yoke further comprising at least one anti-torque bearing adapted to reduce friction thereby facilitating improved calibration of the tire testing machine.

9. The apparatus of claim 8 in which the bearing comprises, in part, a rotatable shaft adapted to interconnect with the spindle extension.

10. The apparatus of claim 9 in which the bearing is positioned upon the upper portion of the strut at a location that is proximate the connection between the low-friction yoke and the strut, whereby the low-friction yoke is capable of spinning upon the bearing with reduced frictional forces being generated in the lateral and longitudinal axis.

11. The apparatus of claim 8 in which the low-friction yoke comprises two arms, further wherein the rotatable shaft comprises a first end and a second end, said first and second ends of the shaft being adapted for articulation with a roller bearing positioned upon at least one arm of the low-friction yoke.

12. An improved tire testing machine adapted for calibration in cooperation with a transducer, wherein the transducer is capable of detecting forces in at least three force directions, further comprising a friction reduction means capable of reducing frictional forces applied along at least two axes, the machine comprising:
    a spindle extension adapted for operable connection to a transducer;
    a frame for supporting said spindle;
    a road simulation belt, the frame supporting said spindle extension in a position above said road simulation belt;
    the spindle extension being aligned along the lateral axis;
    an air bearing operably connected to the spindle extension;
    a load cell strut, the strut being adapted for transmitting forces along the steer axis between the spindle extension and the air bearing; and
    a low friction yoke having a bearing therein which is adapted for reducing the frictional contact between the load cell strut and the spindle extension.

13. The machine of claim 12 in which the anti-torque bearing comprises, in part, a rotatable shaft that passes through the spindle extension.

14. The machine of claim 13 in which the low-friction yoke comprises two arms, further wherein the rotatable shaft comprises a first end and a second end, said first and second ends of the shaft being adapted for articulation with a roller bearing on each arm of the low-friction yoke.

15. The machine of claim 12 in which the bearing is positioned upon the upper surface of the strut at a location that is proximate the connection between the low-friction yoke and the strut, whereby the low-friction yoke is capable of spinning upon the bearing with reduced frictional forces being generated at least two axes.

16. A method of calibrating a flat belt tire testing machine having a transducer connected to a spindle extension, wherein the transducer is capable of measuring load forces in at least three axes while employing a mechanical couple, comprising the steps of:
  (a) providing a frame operably connected to a spindle extension, said spindle extension being the first axis comprising a longitudinal axis, the second axis comprising a lateral axis, and the third axis comprising a steer axis;
  (b) aligning said spindle extension along the lateral axis and in operable connection to the transducer, the spindle extension having a first location along the spindle extension corresponding to the spindle axis/steer axis intersection point and a second location, the second location being positioned a predetermined distance from the first location;
  (c) connecting a first load member to the first location on the spindle extension;
  (d) connecting a second load member to the second location on the spindle extension said first and second load members being positioned in opposite directions;
  (e) applying a first weight to the first load member to generate a first force in a first direction;
  (f) applying a second weight, of equal value to the first weight, to the second load member, thereby generating a second force in a second direction that is opposite to the first force provided in the first direction;
  (g) forming a mechanical couple along the lateral axis; and
  (h) measuring forces generated in the steer axis and longitudinal axis.

17. The method of claim 16 further comprising the step of constructing a matrix of corrective calibration values in both the steer axis and longitudinal axis force directions.

* * * * *